May 23, 1972 C. S. NAKAMURA ET AL Plant Pat. 3,182
APPLE TREE
Filed Jan. 8 1970
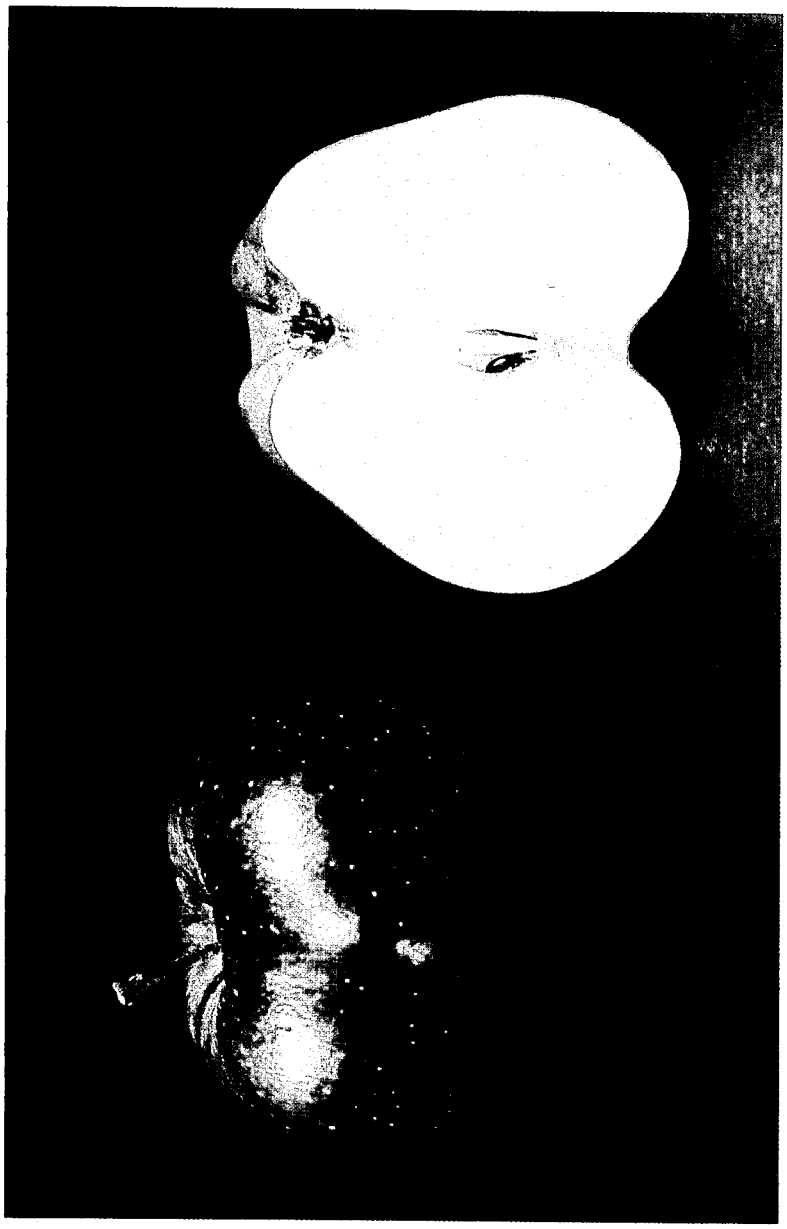
CLIFFORD S. NAKAMURA
MISUYO NAKAMURA
GEORGE NAKAMURA
INVENTORS
BUCKHORN, BLORE, KLARQUIST & SPARKMAN
ATTORNEYS

United States Patent Office

Plant Pat. 3,182
Patented May 23, 1972

3,182
APPLE TREE

Clifford S. Nakamura, Misuyo Nakamura, and George Nakamura, Hood River, Oreg.; said Misuyo Nakamura assignor to said Clifford S. Nakamura and to said George Nakamura, as joint tenants

Filed Jan. 8, 1970, Ser. No. 1,572
Int. Cl. A01h *5/00*
U.S. Cl. Plt.—35 1 Claim

The present invention relates to a new and distinct variety of apple tree which was discovered as a limb sport of the variety commonly known as the Mood Apple (unpatented) which is widely distributed and sold under the registered trademark "Starking." The discovery was made in the Nakamura fruit orchard which is located in Hood River, Oreg.

The discovery occurred as follows: while engaged in thinning fruit of Mood Apple trees in the Nakamura orchard, our attention was attracted by the fruit on one limb of one of the trees. The latter fruit appeared to be distinctly different from the fruit on the remainder of the tree and on other trees of the same variety in the same orchard. Closer and prolonged observation of this particular tree convinced us that the limb bearing the unusual fruit aforementioned, was the result of a bud sport, and we thereupon took prompt steps to preserve the limb and to keep it under close observation.

In due course, we asexually reproduced the new sport by grafting on Mood Apple trees in the Nakamura orchard, and the progeny resulting therefrom, together with continued observations and tests of the original limb sport on the parent tree over a period of years, have conclusively demonstrated that the sport is definitely a new and distinct variety, as particullarly evidenced by the following unique combination of characteristics which are outstanding therein and which distinguish the sport from the standard Mood Apple variety, as well as from all other varieties of which we are aware:

(1) A general resemblance of the fruit to the fruit of the Mood Apple variety, but having a much earlier fruit coloring habit and a habit of developing a full red color approximately a month before maturity;

(2) A striped fruit coloring pattern, with the stripes prominent and distinct in color by the middle of July; and (3) A substantially solid red overall color effect of the fruit color, with relatively obscure stripes of a darker red shade which are hardly noticeable at maturity.

(4) Commences coloring at least two weeks earlier than other Red Delicious apples, and approximately two weeks earlier than the "Topred" Plant Patent 1,916.

This earlier coloring is particularly important in poor coloring seasons, because the absence of frequent warm days and cold nights produces a crop with less color than normal. Thus, our variety by coloring earlier, colors better in poor coloring seasons than other varieties, and thus produces a higher percentage of extra fancy grade fruit than is produced by other trees.

By late August and early September in 1967 the fruit of the new variety had enough color to be classed as extra fancy grade. This was not true of any other tree in our orchards, or for any other Red Delicious trees of which we had knowledge.

As of July 8, 1968, the apples from the new variety had wide red stripes of color appearing over substantially the complete apple (intermixed with green) whereas the apples of the Topred and Mood Apple ("Starking") trees were still distinctly green with little or no red coloring.

The accompanying photograph shows a whole apple and a half apple from the parent tree, with the colors depicted as nearly true as is reasonably possible in color illustration of this character, the colors in the drawing being somewhat lighter than the actual fruit colors due to the high illumination on the subject when photographed.

In the following detailed description of our new variety, color plate designations are from the Color Chart, Royal Horticultural Society (RHS) while the other color names indicate the usual dictionary meaning of the terms.

*The tree*

Locality where grown and observed: Hood River, Oreg.
Dates of first and last pickings: About Sept. 25 and about Oct. 5, respectively.

Tree: Large size; vigorous, spreading; tall; vase-formed; rapid growing; hardy; productive; regular bearer.

- *Trunk.*—Medium stocky; smooth.
- *Branches.*—Medium thickness; smooth; little-branched. Color.—moderate reddish brown. Lenticels—medium few; medium small.
- *Leaves.*—Medium large; medium width; medium length; ovate; taper-pointed; thick; rugose. Average length—3½ inches. Average width—2⅛ inches. Color—Ivy green. Margin—coarsely serrate. Petiole—medium long (1 inch); thick.

Flowers:

- *Dates of first and full bloom.*—About May 4 and May 11, respectively; medium early as compared with other varieties.
- *Color.*—White, with light purplish pink areas on lower (outer) surface near base.

Fruit:

- *Maturity when described.*—Eating ripe.
- *Size.*—Uniform. Axial diameter—about 3⅛ inches. Transverse diameter—about 3 inches.
- *Form.*—Conical; angular.
- *Cavity.*—Symmetrical; flaring; acute; even; pubescent toward apex. Depth—about ¾ inch. Breadth—about 1¼ inch. Markings: color—dark greenish yellow.
- *Basin.*—Symmetrical; rounded; wide-furrowed; pubescent. Depth—about ¼ inch. Breadth—about 1 inch. Markings—none.
- *Stem.*—Stout; pubescent. Length—from about 1 inch to 1⅜ inches. Breadth—about 3/32 inch.
- *Calyx.*—Closed; segments persistent; broadly lanceolate; acute; about ¼ inch long; approximate; prostrate; reflexed from base at apex; both outer and inner surfaces pubescent.
- *Skin.*—Thick; tough; smooth; glossy; waxed. Dots—obscure, many small depressed, circular; color—yellowish pink; distribution—distributed over entire surface, but more numerous toward base. Ground color—red. Markings—striped; bright; color—red.
- *Bloom.*—Wanting.
- *Scarfskin.*—Wanting.
- *Color.*—Striped, deep red all over. The ground color is 46C–RHS, the stripings being slightly redder than 59–60A to 53 (RHS).
- *Flesh.*—Rather juicy. Color—satiny white, with greenish tint. Texture—firm; fine; crisp. Flavor—sub-acid; mild; rich. Aroma—distinct. Quality—good.
- *Core.*—Distant. Bundle area—medium small; cordate; symmetrical at base; acute at base. Halves of core equal. Bundles—inconspicuous; color green. Core lines—clasping. Carpellary area—indistinct; small. Calyx tube—pubescent toward base, funnel form, stem of funnel long; depth of tube to shoulder—about ⅜ inch; entire depth—about ½ inch. Styles—present. Stamens—in one distinct whorl; basal. Seed cells—axile, open; cell walls—thin, tough, length about 13/16 inch; breadth—about 5/16 inch; longitudinal section—obovate; cross section—narrow; surface—fissured, tufted.

*Seeds.*—Average number. Eleven—most cells having 3 seeds. Length—from about 1/4 inch to 3/8 inch. Breadth—about 3/16 inch. Color—Moderate brown.

Use: Market; dessert.

Keeping quality: Good; about 120 days in ordinary storage.

The fruit of our tree differs from that of Patent 2,285 in that the skin of the former is thick and tough while the skin of the latter is of medium thickness and toughness. Also the dots on the skin of the fruit of Patent 2,285 are conspicuous and white, those from our tree being obscure and yellowish.

Our tree differs from that of Plant Patent 2,440 in that the latter has a first bloom about May 1 and a full bloom about May 10, whereas the dates for our trees are May 4 and May 11, respectively. Also the fruit of our tree has good keeping quality of about 120 days in ordinary storage, whereas that of Patent 2,440 is of only medium good quality of about 100 days in ordinary storage.

Our tree differs from that of Patent 2,285 in being spreading instead of upright; of being little-branched instead of much-branched; of flowering medium-early rather than medium-late; and of having a white flower rather than one of pinkish hue.

What is claimed is:

1. A new and distinct variety of apple tree, substantially as herein shown and described, characterized particularly as to novelty by the unique combination of a general resemblance of the fruit to that of the Mood Apple variety (unpatented), but having a much earlier coloring habit, with the coloring developing to a full red color approximately a month before maturity, and commencing to color approximately two weeks before the "Topred" variety, Plant Patent 1,916, developing stripes prominent and distinct in color by the middle of July and having good keeping quality of about 120 days in ordinary storage.

References Cited

UNITED STATES PATENTS

| | | | |
|---|---|---|---|
| P.P. 1,411 | 8/1955 | Brauns | Plants—35 |
| P.P. 2,285 | 9/1963 | Gould | Plants—35 |
| P.P. 2,440 | 8/1964 | Rypczynski | Plants—35 |

ROBERT E. BAGWILL, Primary Examiner